(12) United States Patent
Cole et al.

(10) Patent No.: US 10,137,116 B2
(45) Date of Patent: Nov. 27, 2018

(54) BENZIMIDAZOLE SULFIDE DERIVATIVES FOR THE TREATMENT OR PREVENTION OF TUBERCULOSIS

(71) Applicant: École Polytechnique Fédérale de Lausanne (EPFL), Lausanne (CH)

(72) Inventors: Stewart Cole, Écublens (CH); Jan Lars Rybniker, Cologne (DE)

(73) Assignee: École Polytechnique Fédérale de Lausanne (EPFL), Lausanne (CH)

( * ) Notice: Subject to any disclaimer, the term of this patent is extended or adjusted under 35 U.S.C. 154(b) by 0 days.

(21) Appl. No.: 15/546,680

(22) PCT Filed: Jan. 26, 2016

(86) PCT No.: PCT/EP2016/051549
§ 371 (c)(1),
(2) Date: Jul. 27, 2017

(87) PCT Pub. No.: WO2016/120259
PCT Pub. Date: Aug. 4, 2016

(65) Prior Publication Data
US 2018/0028517 A1 Feb. 1, 2018

(30) Foreign Application Priority Data
Jan. 27, 2015 (EP) .................................... 15152650

(51) Int. Cl.
*A61P 31/06* (2006.01)
*A61K 31/443* (2006.01)
*A61K 31/4439* (2006.01)
*A61K 45/06* (2006.01)
*C07D 401/12* (2006.01)

(52) U.S. Cl.
CPC .......... *A61K 31/4439* (2013.01); *A61K 45/06* (2013.01); *A61P 31/06* (2018.01); *C07D 401/12* (2013.01); *A61K 2300/00* (2013.01)

(58) Field of Classification Search
CPC ........................... A61K 31/4439; A61P 31/06
See application file for complete search history.

(56) References Cited

U.S. PATENT DOCUMENTS

2003/0069279 A1\* 4/2003 Sato ..................... A61K 31/165
514/338

FOREIGN PATENT DOCUMENTS

| EP | 2548555 A1 \* | 1/2013 | ......... A61K 31/4439 |
|----|---|---|---|
| GB | 1234058 A | 6/1971 | |
| WO | WO-2004036224 A2 | 4/2004 | |
| WO | WO-2015009883 A1 | 1/2015 | |

OTHER PUBLICATIONS

Rybniker et al. "Lansoprazole is an antituberculous prodrug targeting cytochrome bc1," Nature. 6:7659: 1-8 (2015).
Suzuki et al. "Effect of proton pump inhibitor alone or in combination with clarithromycin on mycobacterial growth in human alveolar macrophages," FEMS Microbiol Lett. 182(1) 69-72 (2000).
Klimesová et al. "New benzimidazole derivatives as antimycobacterial agents," Il Farmaco. 57(4): 259-65 (2002).
International Search Report for International Patent Application No. PCT/EP2016/051549, dated Apr. 8, 2016 (4 pages).
Written Opinion for International Patent Application No. PCT/EP2016/051549, dated Apr. 8, 2016 (6 pages).

\* cited by examiner

*Primary Examiner* — Theodore R. West
(74) *Attorney, Agent, or Firm* — Clark & Elbing LLP

(57) ABSTRACT

The present invention relates to the use of benzimidazole sulfide derivatives and prodrugs thereof in the treatment and/or prevention of tuberculosis.

11 Claims, 8 Drawing Sheets

BENZIMIDAZOLE SULFIDE DERIVATIVES FOR THE TREATMENT OR PREVENTION OF TUBERCULOSIS

TECHNICAL FIELD

The present invention relates to the use of benzimidazole sulfide derivatives and prodrugs thereof in the treatment and/or prevention of tuberculosis.

BACKGROUND OF THE INVENTION

Tuberculosis resulting from infection with *Mycobacterium tuberculosis* (Mtb) is a serious global health problem accounting for 1.4 million deaths in 2011. A major reason for the high morbidity and mortality caused by Mtb is the long duration of therapy and increasing multidrug-resistance of *Mycobacterium* strains.

Mtb has been treated with combination therapy for over fifty years. Anti-tuberculous first line oral drugs used in the treatment of Mtb are principally Ethambutol (EMB), Isoniazid (INH), Pyrazinamide (PZA), Rifampicin (RMP), Rifampin (RIP) and Rifabutin (RFB).

Reports of high rates of multidrug-resistant tuberculosis (MDR-TB) and extensively drug-resistant tuberculosis (XDR-TB) in recent years have highlighted the failure of Mtb therapy. According to the latest WHO statistics, approximately half a million new cases of MDR-TB are diagnosed every year. Of these, it is estimated that approximately 40,000 have extensively drug-resistant tuberculosis (XDR-TB).

MDR-TB is defined as resistance to at least Isoniazid and Rifampicin, the two most effective first-line antituberculous drugs. The treatment regimen for MDR-TB comprises a later generation fluoroquinolone (moxifloxacin, gatifloxacin, or levofloxacin), an injectable aminoglycosides (either amikacin, kanamycin), any first-line drug to which the isolate is susceptible, and the addition of drugs such as cycloserine/terizidone and ethionamide. XDR-TB, in addition to the resistance observed for MDR-TB, is defined by a resistance to any fluoroquinolone and any injectable second line aminoglycoside drug. Thus, the design of a treatment regimen for XDR-TB is more complex.

Importantly, these drugs are less effective, more expensive, more toxic and require longer course of treatment than drugs used in the treatment of susceptible organisms.

Therefore, there is a need for novel highly effective and specific compounds to combat Mtb, MDR-TB and XDR-TB with fewer adverse reactions.

SUMMARY OF THE INVENTION

The present invention provides a benzimidazole sulfide derivative of general formula (I):

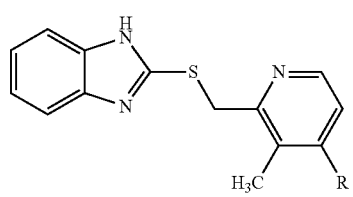

wherein R is selected from the group comprising hydrogen, $C_1$-$C_6$-alkyl, $C_1$-$C_6$-heteroalkyl, $C_1$-$C_6$-haloalkyl, aryl, $C_1$-$C_6$-alkyl aryl, heteroaryl, $C_1$-$C_6$-alkyl heteroaryl, $C_2$-$C_6$-alkenyl, $C_2$-$C_6$-alkenyl aryl, $C_2$-$C_6$-alkenyl heteroaryl, $C_3$-$C_8$-cycloalkyl, $C_1$-$C_6$-alkyl cycloalkyl, heterocycloalkyl, $C_1$-$C_6$-alkyl heterocycloalkyl, carboxy, $C_1$-$C_6$-alkyl carboxy, acyl, $C_1$-$C_6$-alkyl acyl, acyloxy, $C_1$-$C_6$-alkyl acyloxy, $C_1$-$C_6$-alkoxy, $C_1$-$C_6$-heteroalkoxy, $C_1$-$C_6$-haloalkoxy, $C_1$-$C_6$-alkoxycarbonyl, halogen, sulfanyl, and $C_1$-$C_6$-alkylsulfanyl, and its pharmaceutically acceptable salts, and/or mixtures thereof for use in the treatment and/or prevention of tuberculosis.

The invention also provides a pharmaceutical composition comprising said benzimidazole sulfide derivative and a pharmaceutically acceptable carrier, diluent or excipient for use in the treatment and/or prevention of tuberculosis.

The invention further relates to a prodrug of general formula (II):

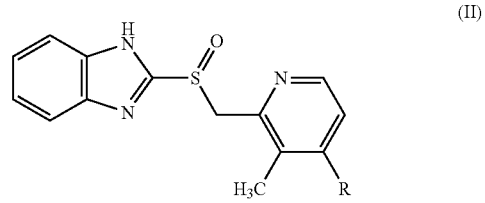

wherein R is selected from the group comprising hydrogen, $C_1$-$C_6$-alkyl, $C_1$-$C_6$-heteroalkyl, $C_1$-$C_6$-haloalkyl, aryl, $C_1$-$C_6$-alkyl aryl, heteroaryl, $C_1$-$C_6$-alkyl heteroaryl, $C_2$-$C_6$-alkenyl, $C_2$-$C_6$-alkenyl aryl, $C_2$-$C_6$-alkenyl heteroaryl, $C_3$-$C_8$-cycloalkyl, $C_1$-$C_6$-alkyl cycloalkyl, heterocycloalkyl, $C_1$-$C_6$-alkyl heterocycloalkyl, carboxy, $C_1$-$C_6$-alkyl carboxy, acyl, $C_1$-$C_6$-alkyl acyl, acyloxy, $C_1$-$C_6$-alkyl acyloxy, $C_1$-$C_6$-alkoxy, $C_1$-$C_6$-heteroalkoxy, $C_1$-$C_6$-haloalkoxy, $C_1$-$C_6$-alkoxycarbonyl, halogen, sulfanyl, and $C_1$-$C_6$-alkylsulfanyl, and its pharmaceutically acceptable salts, enantiomers and/or mixtures thereof for use in the treatment and/or prevention of tuberculosis.

It also provides a pharmaceutical composition comprising said prodrug of general formula (II) and a pharmaceutically acceptable carrier, diluent or excipient for use in the treatment and/or prevention of tuberculosis.

DETAILED DESCRIPTION OF THE INVENTION

Figure 1:
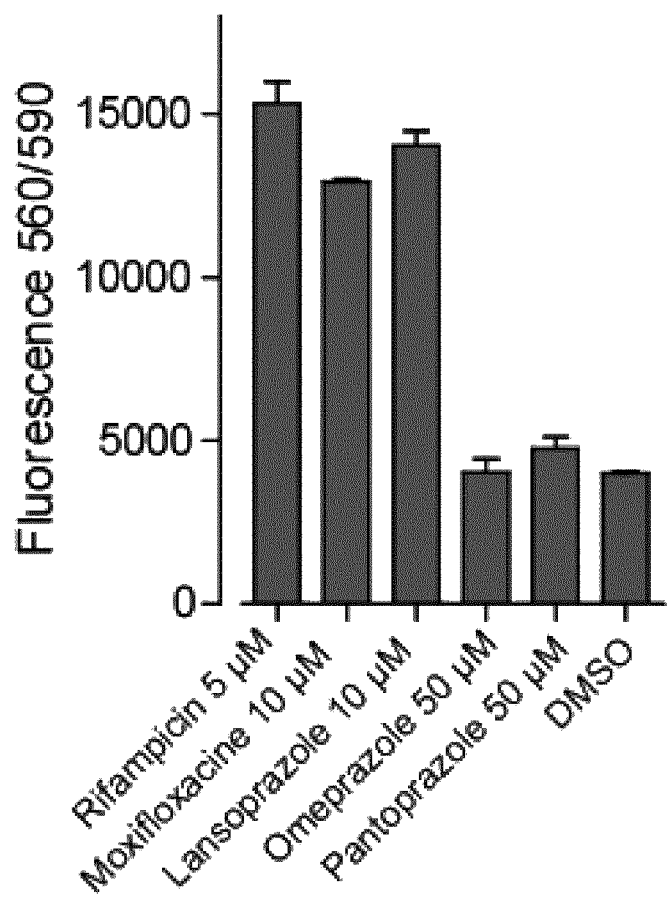
FIG. 1. Ex vivo and in vitro activity of LPZ. Protective activity of LPZ and other drugs (Rifampicin, Moxifloxacine, Omeprazole, Pantoprazole and DMSO as control) against Mtb induced killing of MRC-5 lung fibroblasts. Data are expressed as the mean±SD of triplicates. Fibroblasts were quantified three days after Mtb infection using Prestoblue.

The present invention relates to a benzimidazole sulfide derivative of general formula (I):

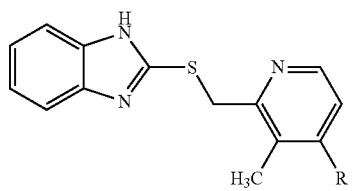

wherein R is selected from the group comprising hydrogen, $C_1$-$C_6$-alkyl, $C_1$-$C_6$-heteroalkyl, $C_1$-$C_6$-haloalkyl, aryl, $C_1$-$C_6$-alkyl aryl, heteroaryl, $C_1$-$C_6$-alkyl heteroaryl, $C_2$-$C_6$-alkenyl, $C_2$-$C_6$-alkenyl aryl, $C_2$-$C_6$-alkenyl heteroaryl, $C_3$-$C_8$-cycloalkyl, $C_1$-$C_6$-alkyl cycloalkyl, heterocycloalkyl, $C_1$-$C_6$-alkyl heterocycloalkyl, carboxy, $C_1$-$C_6$-alkyl carboxy, acyl, $C_1$-$C_6$-alkyl acyl, acyloxy, $C_1$-$C_6$-alkyl acyloxy, $C_1$-$C_6$-alkoxy, $C_1$-$C_6$-heteroalkoxy, $C_1$-$C_6$-haloalkoxy, $C_1$-$C_6$-alkoxycarbonyl, halogen, sulfanyl, and $C_1$-$C_6$-alkylsulfanyl, and its pharmaceutically acceptable salts, and/or mixtures thereof for use in the treatment and/or prevention of tuberculosis.

The following definitions are supplied in order to facilitate the understanding of the present invention.

As used herein, the term "comprise" is generally used in the sense of include, that is to say permitting the presence of one or more features or components.

As used herein, the singular form "a", "an" and "the" include plural references unless the context clearly dictates otherwise.

The following paragraphs provide definitions of the various chemical moieties that make up the compounds according to the invention and are intended to apply uniformly throughout the specification and claims unless an otherwise expressly set out definition provides a broader definition.

"$C_1$-$C_6$ alkyl" refers to monovalent straight-chained and branched alkyl groups having 1 to 6 carbon atoms. This term is exemplified by groups such as methyl, ethyl, n-propyl, isopropyl, n-butyl, isobutyl, tert-butyl, n-hexyl and the like.

"$C_1$-$C_6$-heteroalkyl" includes both straight-chained and branched $C_1$-$C_6$ alkyl groups according to the definition above, having at least one or more heteroatoms selected from S, O and N.

"$C_1$-$C_6$-haloalkyl" includes both straight-chained and branched $C_1$-$C_6$ alkyl groups according to the definition above, having at least one or more halogen selected from F, Cl, Br or I.

"Aryl" refers to an unsaturated aromatic carbocyclic group of from 6 to 14 carbon atoms having a single ring (e.g., phenyl) or multiple condensed rings (e.g., naphthyl). Preferred aryl include phenyl, naphthyl, phenantrenyl and the like.

"$C_1$-$C_6$ alkyl aryl" refers to $C_1$-$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted, pyrrolyl, pyridyl furyl, thienyl, imidazolyl, oxazolyl, isoxazolyl, thiazolyl, isothiazolyl, pyrazolyl. Preferred heteroaromatic groups is selected from the group comprising pyrrolyl.

"$C_1$-$C_6$ alkyl heteroaryl" refers to $C_1$-$C_6$-alkyl groups having a heteroaryl substituent. Preferred heteroaryl substituent is selected from the group comprising pyrrolyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH=CH2), n-2-propenyl (allyl, —CH2CH=CH2) and the like.

"$C_2$-$C_6$-alkenyl aryl" refers to $C_2$-$C_6$-alkenyl groups having an aryl substituent, including 2-phenylvinyl and the like.

"$C_2$-$C_6$-alkenyl heteroaryl" refers to $C_2$-$C_6$-alkenyl groups having a heteroaryl substituent, including 2-(3-pyridinyl)vinyl and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). Preferred cycloalkyl include cyclopentyl, cyclohexyl, norbornyl and the like.

"$C_1$-$C_6$-alkyl cycloalkyl" refers to $C_1$-$C_6$-alkyl groups having a cycloalkyl substituent, including cyclohexylmethyl, cyclopentylpropyl, and the like.

"Heterocycloalkyl" refers to $C_3$-$C_8$-cycloalkyl group according to the definition above, in which up to 3 carbon atoms are replaced by heteroatoms chosen from the group consisting of O, S, NR, R being defined as hydrogen or methyl. Preferred heterocycloalkyl include pyrrolidine, piperidine, piperazine, 1-methylpiperazine, morpholine, and the like.

"$C_1$-$C_6$-alkyl heterocycloalkyl" refers to $C_1$-$C_6$-alkyl groups having a heterocycloalkyl substituent, including 2-(1-pyrrolidinyl)ethyl, 4-morpholinylmethyl, (1-methyl-4-piperidinyl)methyl and the like.

"Carboxy" refers to the group —C(O)OH.

"$C_1$-$C_6$-alkyl carboxy" refers to $C_1$-$C_5$-alkyl groups having a carboxy substituent, including 2-carboxyethyl and the like.

"Acyl" refers to the group —C(O)R where R includes "C$_1$-C$_6$-alkyl", "aryl", "heteroaryl", "C$_1$-C$_6$-alkyl aryl" or "C$_1$-C$_6$-alkyl heteroaryl".

"C$_1$-C$_6$-alkyl acyl" refers to C$_1$-C$_6$-alkyl groups having an acyl substituent, including 2-acetylethyl and the like.

"Acyloxy" refers to the group —OC(O)R' where R' includes "C$_1$-C$_6$-alkyl", "aryl", "heteroaryl", "C$_1$-C$_6$-alkyl aryl" or "C$_1$-C$_6$-alkyl heteroaryl".

"C$_1$-C$_6$-alkyl acyloxy" refers to C$_1$-C$_6$-alkyl groups having an acyloxy substituent, including 2-(acetyloxy)ethyl and the like.

"C$_1$-C$_6$-alkoxy" refers to group —O—R' where R' includes both straight-chained and branched "C$_1$-C$_6$-alkyl" or "C$_1$-C$_6$-haloalkyl" or "C$_1$-C$_6$-heteroalkyl" or "aryl" or "hetero-aryl" or "C$_1$-C$_6$-alkyl aryl" or "C$_1$-C$_6$-alkyl heteroaryl". Preferred alkoxy groups include by way of example, methoxy, ethoxy, propoxy, butoxy, phenoxy and the like.

"C$_1$-C$_6$-heteroalkoxy" refers to both straight-chained and branched C$_1$-C$_6$-alkoxy group according to the definition above, having at least one or more heteroatoms selected from S, O and N.

"C$_1$-C$_6$-haloalkoxy" refers to refers to both straight-chained and branched C$_1$-C$_6$-alkoxy group according to the definition above, having at least one or more halogen selected from F, Cl, Br or I.

"C$_1$-C$_6$-alkoxycarbonyl" refers to the group —C(O)OR' where R' includes H, "C$_1$-C$_6$-alkyl" or "aryl" or "heteroaryl" or "C$_1$-C$_6$-alkyl aryl" or "C$_1$-C$_6$-alkyl heteroaryl".

"Halogen" refers to fluoro, chloro, bromo and iodo atoms.

"Sulfanyl" refers to groups —S—R where R includes "C$_1$-C$_6$-alkyl" or "aryl" or "hetero-aryl" or "C$_1$-C$_6$-alkyl aryl" or "C$_1$-C$_6$-alkyl heteroaryl". Preferred sulfanyl groups include methylsulfanyl, ethylsulfanyl, and the like.

"C$_1$-C$_6$-alkylsulfanyl" refers to C$_1$-C$_6$-alkyl groups having a sulfanyl substituent.

"Substituted or unsubstituted": Unless otherwise constrained by the definition of the individual substituent, the above set out groups, like "alkyl", "alkoxy", "alkenyl", "alkynyl", "aryl", "amine", "benzene" and "heteroaryl" etc. groups can optionally be substituted with from 1 to 5 substituents selected from the group consisting of "C$_1$-C$_6$-alkyl", "C$_2$-C$_6$-alkenyl", "C$_2$-C$_6$-alkynyl", "cycloalkyl", "heterocycloalkyl", "C$_1$-C$_6$-alkyl aryl", "halo C$_1$-C$_6$-alkyl aryl", "C$_1$-C$_6$-alkyl heteroaryl", "C$_1$-C$_6$-alkyl cycloalkyl", "C$_1$-C$_6$-alkyl heterocycloalkyl", "amine", "amino", "ammonium", "acyl", "acyloxy", "acylamino", "aminocarbonyl", "alkoxycarbonyl", "ureido", "carbamate", "aryl", "heteroaryl", "thioalkyl", "sulfmyl", "sulfonyl", "alkoxy", "sulfanyl", "halogen", "haloalkyl", "carboxy", "trihalomethyl", "cyano", "hydroxyl", "mercapto", "nitro", and the like.

The present invention also relates to a benzimidazole sulfide derivative of general formula (I):

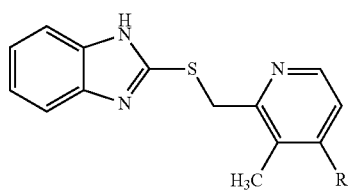

(I)

wherein R is selected from the group comprising C$_1$-C$_6$-alkyl, C$_1$-C$_6$-heteroalkyl, C$_1$-C$_6$-haloalkyl, C$_1$-C$_6$-alkoxy, C$_1$-C$_6$-heteroalkoxy, C$_1$-C$_6$-haloalkoxy, and halogen, and its pharmaceutically acceptable salts, and/or mixtures thereof for use in the treatment and/or prevention of tuberculosis.

Alternatively, the present invention relates to a benzimidazole sulfide derivative of general formula (I):

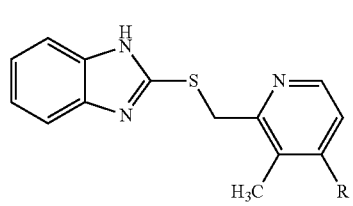

(I)

wherein R is selected from the group comprising C$_1$-C$_6$-alkoxy, C$_1$-C$_6$-heteroalkoxy, C$_1$-C$_6$-haloalkoxy, and halogen, and its pharmaceutically acceptable salts, and/or mixtures thereof for use in the treatment and/or prevention of tuberculosis.

Preferably, the benzimidazole sulfide derivative of general formula (I) is selected from the group comprising:

Lanzoprazole sulfide (LPZS):

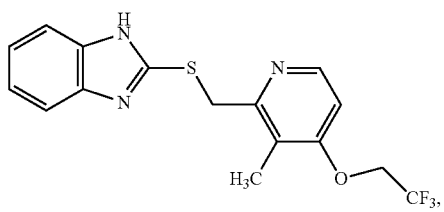 [SMILES: Cc1c(OCC(F)(F)F)ccnc1CSc1nc2ccccc2[nH]1]

Rabeprazole sulfide:

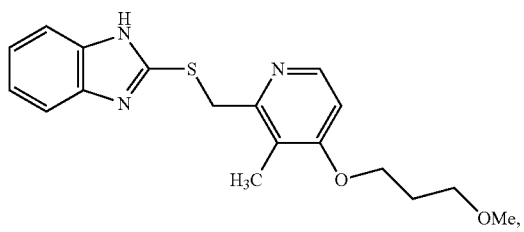 [SMILES: COCCCOc1ccnc(CSc2nc3ccccc3[nH]2)c1C]

4-Desmethoxypropoxyl-4-chloro rabebrazole sulfide:

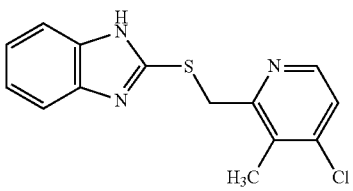 [SMILES: Cc1c(Cl)ccnc1CSc1nc2ccccc2[nH]1]

their pharmaceutically acceptable salts, and/or mixtures thereof for use in the treatment and/or prevention of tuberculosis.

Most preferably, the benzimidazole sulfide derivative of general formula (I) is Lanzoprazole sulfide (LPZS):

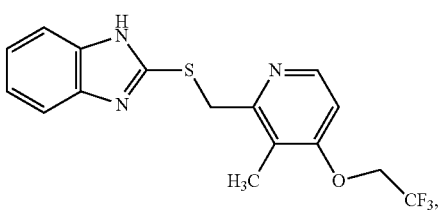

its pharmaceutically acceptable salts, and/or mixtures thereof for use in the treatment and/or prevention of tuberculosis.

The invention also relates to salts of the benzimidazole sulfide derivatives of general formula (I), chemical modified compounds, and mixtures thereof. Preferably, these salts are pharmaceutically acceptable. According to the present invention, pharmaceutically acceptable salts are produced from acidic inorganic or organic compounds, or alkaline inorganic or organic compounds. As used herein, the phrase "pharmaceutically acceptable salt" refers to a salt that retains the biological effectiveness of the free acids and bases of a specified compound and that is not biologically or otherwise undesirable.

Interestingly, the present invention provides benzimidazole sulfide derivatives of general formula (I) for use in the treatment and/or prevention of tuberculosis, wherein said benzimidazole sulfide derivatives are inhibitors of Mtb, and have an IC50 less than about 50 μM, preferably less than about 20 μM, more preferably less than about 15 μM.

As used herein, the term "inhibitor" refers to compounds that block or partially block directly or indirectly the mycobacterial growth.

As used herein, the term "IC50" represents the concentration of a drug that is required for 50% inhibition.

As used herein, the term "about" applies to numeric values and refers to a range of numbers that one of skill in the art would consider equivalent to the recited values. For example, "about 20 μM" refers to 20 μM+/−10%.

As shown in the examples, Lanzoprazole sulfide (LPZS) has an IC50 of 0.460 μM, Rabeprazole sulfide has an IC50 of 5 μM and 4-Desmethoxypropoxyl-4-chloro rabebrazole sulfide has an IC50 of 6-12 μM (Example 4).

Thus, the present invention provides benzimidazole sulfide derivatives of general formula (I) for use in the treatment and/or prevention of tuberculosis, wherein tuberculosis is caused by bacterial strains selected from the group comprising mycobacterial strains, and multi-drug resistant strains of *mycobacterium*.

Advantageously, the benzimidazole sulfide derivatives of general formula (I) are highly specific inhibitors of mycobacterial strains and multi-drug resistant strains of *mycobacterium*, wherein the MIC of said inhibitors is less than about 20 μM, preferably less than about 10 μM.

As used herein, the term "minimum inhibitory concentration" or "MIC" is the lowest concentration of a drug that will inhibit the visible growth of a microorganism after overnight incubation.

As shown in the examples, the benzimidazole sulfide derivatives of formula (I), preferably lansoprazole sulfate LPZS, inhibit specifically the growth of *mycobacterium tuberculosis* strains selected from the group comprising *M. Tuberculosis* H37Rv, *M. Tuberculosis* Erdman and *M. Tuberculosis* HN878 and the growth of multi-drug resistant strains of *mycobacterium* selected from the group comprising *M. Tuberculosis* 59744, *M. Tuberculosis* MB3649, *M. Tuberculosis* MI1020, *M. Tuberculosis* 43061, *M. Tuberculosis* 45776, and *M. Tuberculosis* 49975. In particular, LPZS has a highly Mtb-selective activity against mycobacterial strains, and multi-drug resistant strains of *mycobacterium* wherein the MIC is less than about 2 μM (Table 3 and 4).

Furthermore, the present invention provides benzimidazole sulfide derivatives of formula (I) for use in the treatment and/or prevention of tuberculosis, wherein the concentration in blood of said benzimidazole sulfide derivatives is at least 50% of Cmax, preferably at least 60% of Cmax, more preferably at least 70% of Cmax at 0.5 h after administration.

"Cmax" as used herein refers to the peak plasma concentration of a drug after administration wherein the concentration is the amount of drug in a given volume of plasma.

Figure 5:
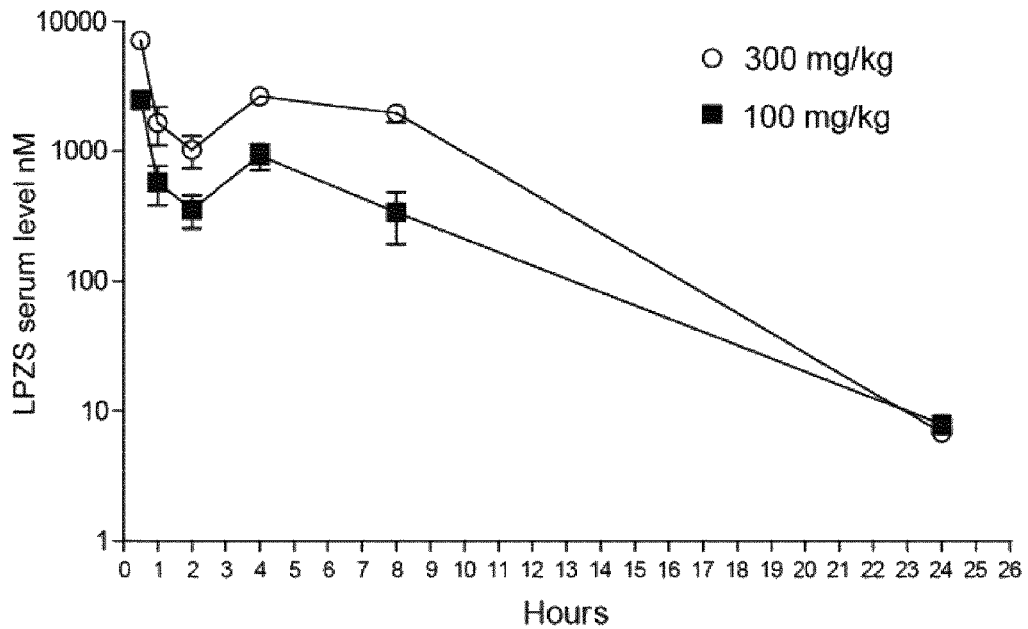
FIG. 5. Pharmacokinetics of LPZS. BALB/c mice were given 100 mg/kg or 300 mg/kg of LPZS by oral gavage and serum levels were determined after 0.5, 1, 2, 4, 8 and 24 hours. LPZS shows non-linear pharmacokinetics with a second peak after approximately 4 hours of administration.

As shown in the examples, the concentration in blood of the benzimidazole sulfide derivative of formula I, lansoprazole sulfate LPZS, is 100% of Cmax at 0.5 h after administration (Example 9, FIG. 5).

Thus, the pharmacokinetic profile of the benzimidazole sulfide derivatives of general formula (I) is favorable for a fast onset of action of these compounds.

As used herein, the term "onset of action" refers to the time required after administration of a drug to become effective.

The present invention also relates to a compound of general formula (II) that is a "prodrug" of a benzimidazole sulfide derivative of general formula (I). Any of the benzimidazole sulfide derivatives of general formula (I) described herein can be administered as a prodrug of general formula (II).

As used herein, the term "prodrug" refers to a compound that is converted in vitro or through a normal metabolic process in vivo by a reaction with an enzyme, gastric acid or the like under a physiological condition in the living body, e.g. by oxidation, reduction, hydrolysis or the like, each of which is carried out enzymatically.

Thus, the present invention relates to a compound of general formula (II)

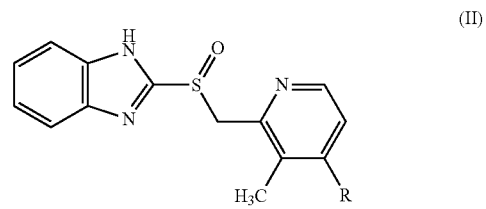

(II)

wherein R is selected from the group comprising hydrogen, $C_1$-$C_6$-alkyl, $C_1$-$C_6$-heteroalkyl, $C_1$-$C_6$-haloalkyl, aryl, $C_1$-$C_6$-alkyl aryl, heteroaryl, $C_1$-$C_6$-alkyl heteroaryl, $C_2$-$C_6$-alkenyl, $C_2$-$C_6$-alkenyl aryl, $C_2$-$C_6$-alkenyl heteroaryl, $C_3$-$C_8$-cycloalkyl, $C_1$-$C_6$-alkyl cycloalkyl, heterocycloalkyl, $C_1$-$C_6$-alkyl heterocycloalkyl, carboxy, $C_1$-$C_6$-alkyl carboxy, acyl, $C_1$-$C_6$-alkyl acyl, acyloxy, $C_1$-$C_6$-alkyl acyloxy, $C_1$-$C_6$-alkoxy, $C_1$-$C_6$-heteroalkoxy, $C_1$-$C_6$-haloalkoxy, $C_1$-$C_6$-alkoxycarbonyl, halogen, sulfanyl, and $C_1$-$C_6$-alkyl-sulfanyl, and its pharmaceutically acceptable salts, enantiomers and/or mixtures thereof for use in the treatment and/or prevention of tuberculosis.

Preferably, the compound of general formula (II) is selected from the group comprising:

(RS)-2-([3-méthyl-4-(2,2,2-trifluoroéthoxy)pyridin-2-yl]méthylsulfinyl)-1H-benzimidazole (Lansoprazole):

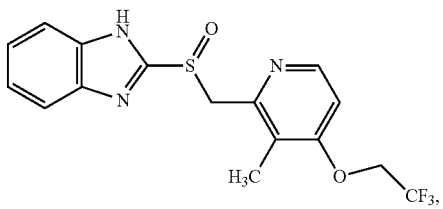 [SMILES: Cc1c(OCC(F)(F)F)ccnc1CS(=O)c1nc2ccccc2[nH]1]

(RS)-2-([4-(3-méthoxypropoxy)-3-méthylpyridin-2-yl]méthylsulfinyl)-1H-benzimidazole (Rabeprazole):

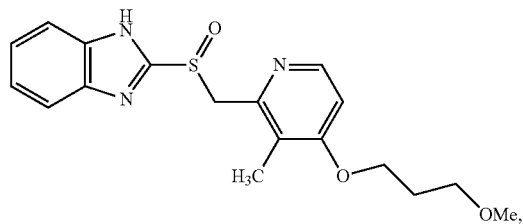 [SMILES: COCCCOc1ccnc(CS(=O)c2nc3ccccc3[nH]2)c1C]

(RS)-4-Desmethoxypropoxyl-4-chloro Rabeprazole:

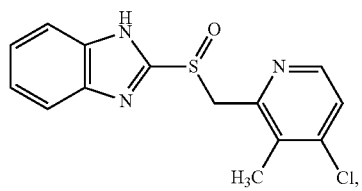 [SMILES: Cc1c(Cl)ccnc1CS(=O)c1nc2ccccc2[nH]1]

their pharmaceutically acceptable salts, enantiomers and/or mixtures thereof for use in the treatment and/or prevention of tuberculosis.

Most preferably, the compound of general formula (II) is (RS)-2-([3-méthyl-4-(2,2,2-trifluoroéthoxy)pyridin-2-yl]méthylsulfinyl)-1H-benzimidazole (Lansoprazole):

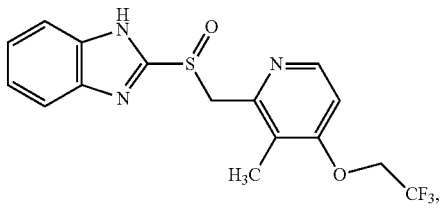

its pharmaceutically acceptable salts, enantiomers and/or mixtures thereof for use in the treatment and/or prevention of tuberculosis.

Lansoprazole and Rabeprazole are well known proton pump inhibitors (PPIs) including also Omeprazole and Pantoprazole, that are used in the treatment of gastroesophageal reflux disease, peptic ulcer disease as well as the eradication of *Helicobacter pylori* as a part of combination regimens. They are substituted benzimidazoles that contain the asymmetric chiral sulfur atom in their chemical structure and therefore they exist in form R and S-enantiomers.

Interestingly, it has been found that compounds of formula (II), their pharmaceutically acceptable salts, enantiomers and/or mixtures thereof are inhibitors of Mtb and have an IC50 less than about 50 µM, preferably less than about 40 µM.

Figure 3A:
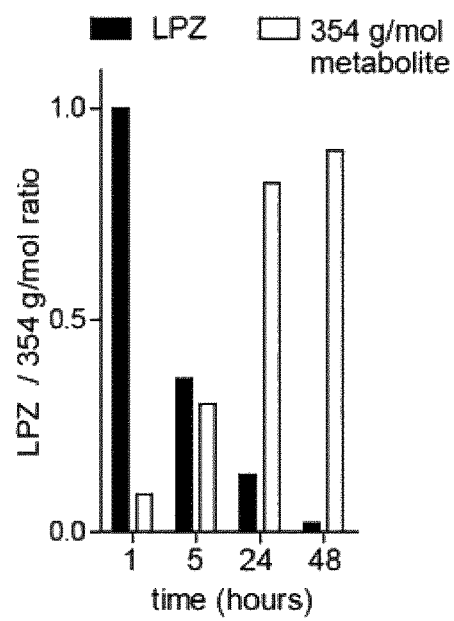
FIG. 3. LPZ is a prodrug that is converted to LPZS in an intracellular environment. A) Intracellular ratio of LPZ and the metabolite of smaller mass (approx. 354 g/mol) determined by electrospray ionisation mass spectrometry (ESI-MS) over a 48 hour period in MRC-5 cells. Representative example of three individual experiments. B) Extracted MS spectrum of ESI-MS experiments performed on the cell lysate of MRC-5 fibroblasts exposed to LPZ. C) LPZ/LPZS ratio determined by ESI-MS over a 48 hour period in 7H9 broth. Representative example of three individual experiments. D) Dose-response curve of LPZS for Mtb grown in 7H9 broth. E) Survival of Mtb infected MRC-5 fibroblasts at different concentrations of LPZS.
Figure 3B:
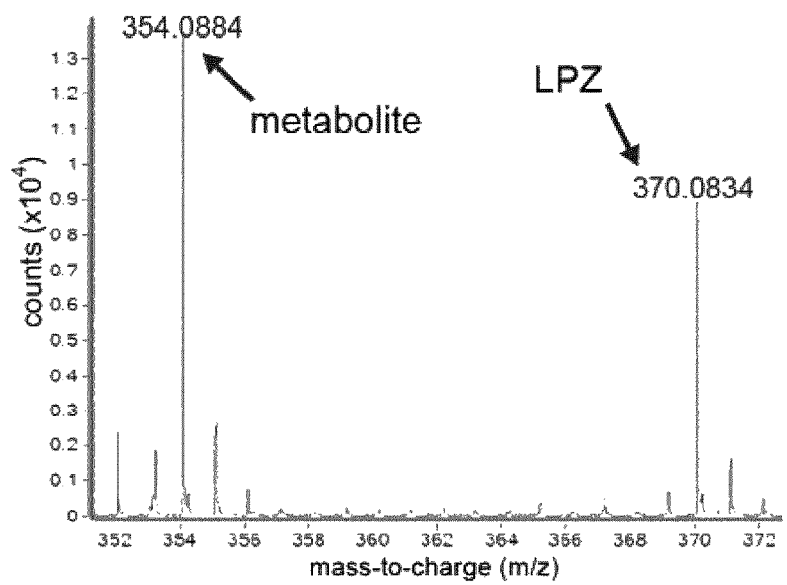
Figure 3C:
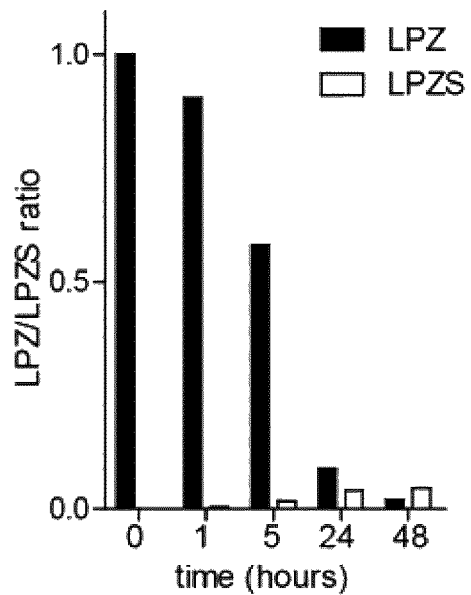

The compound of formula (II) Lansoprazole (LPZ) can be considered as a prodrug of Lansoprazole Sulfide (LPZS) (FIG. 3A-C). As shown in the example, LPZ inhibits the growth of Mtb as well as Rifampicin or Moxifloxacine in contrast to Omeprazole and Pantoprazole that are not compounds of formula II (FIG. 1). Furthermore, it has been shown that LPZ has an IC50 of 32.8 µM, the enantiomers R-Lansoprazole and S-Lansoprazole have a similar IC50 and the salt Rabeprazole sodium has an IC50 of 25 µM (Example 5, Table 2).

The present invention further relates to a pharmaceutical composition comprising the benzimidazole sulfide derivative of formula (I) and a pharmaceutically acceptable carrier, diluent or excipient for use in the treatment and/or prevention of tuberculosis.

It also relates to a pharmaceutical composition comprising the compound of general formula (II) and a pharmaceutically acceptable carrier, diluent or excipient for use in the treatment and/or prevention of tuberculosis.

As to the appropriate carriers, reference may be made to the standard literature describing these, e.g. to chapter 25.2 of Vol. 5 of "Comprehensive Medicinal Chemistry", Pergamon Press 1990, and to "Lexikon der Hilfsstoffe für Pharmazie, Kosmetik und angrenzende Gebiete", by H. P. Fiedler, Editio Cantor, 2002. The term "pharmaceutically acceptable carrier" means a carrier or excipient that is useful in preparing a pharmaceutical composition that is generally safe, and possesses acceptable toxicities. Acceptable carriers include those that are acceptable for veterinary use as well as human pharmaceutical use. A "pharmaceutically acceptable carrier" as used in the specification and claims includes both one and more than one such carrier.

The compounds of the invention, namely benzimidazole sulfide derivatives of formula (I), and/or compounds of general formula (II) that are used in the treatment and/or prevention of tuberculosis can be incorporated into a variety of formulations and medicaments for therapeutic administration. More particularly, one or more compound(s) as provided herein can be formulated into pharmaceutical compositions by combination with appropriate, pharmaceutically acceptable carriers, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the compounds can be achieved in various ways, including oral, buccal, rectal, parenteral, intraperitoneal, intradermal, transdermal, intracranial and/or intratracheal administration. Moreover, the compound can be administered in a local rather than systemic manner, in a depot or sustained release formulation. The compounds can be formulated with common excipients, diluents or carriers, and compressed into tablets, or formulated as elixirs or solutions for convenient oral administration, or administered by the intramuscular or intravenous routes. The compounds can be administered transdermally, and can be formulated as sustained release dosage forms and the like. The compounds can be administered alone, in combination with each other, or they can be used in combination with other known compounds. Suitable formulations for use in the present invention are found in Remington's Pharmaceutical Sciences (Mack Publishing Company (1985) Philadelphia, Pa., 17th ed.), which is incorporated herein by reference. Moreover, for a brief review of methods for drug delivery, see, Langer, Science (1990) 249:1527-1533, which is incorporated herein by reference.

The amount of a compound as provided herein that can be combined with a carrier material to produce a single dosage form will vary depending upon the disease treated, the subject in need thereof, and the particular mode of administration. However, as a general guide, suitable unit doses for the compounds of the present invention can, for example, preferably contain between 0.1 mg to about 1000 mg, between 1 mg to about 500 mg, and between 1 mg to about 300 mg of the active compound. In another example, the unit dose is between 1 mg to about 100 mg. Such unit doses can be administered more than once a day, for example, 2, 3, 4, 5 or 6 times a day, but preferably 1 or 2 times per day, so that the total dosage for a 70 kg human adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area. A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release. It can be necessary to use dosages outside these ranges in some cases as will be apparent to those skilled in the art.

Alternatively, the pharmaceutical composition comprising the benzimidazole sulfide derivative of formula (I), and/or the compound of general formula (II) and a pharmaceutically acceptable carrier, diluent or excipient for use in the treatment and/or prevention of tuberculosis, further comprises at least one or more additional agents effective against tuberculosis infection.

Preferably, the at least one or more additional agents effective against tuberculosis infection is selected from the group comprising rifampin, moxifloxacin, isoniazid, rifapentine, rifabutin, pyrazinamide, ethambutol, streptomycin, kanamycin, amikacin, gatifloxacin, levofloxacin, ofloxacin, ciprofloxacin, capreomycin, ethionamide, cycloserine, para-aminosalicylic acid, thiacetazone, clarithromycin, amoxicillin-clavulanic acid, imipenem, meropenem, viomycin, terizidone, TMC207, PA-824, OPC-7683, LL-3858 and SQ-109.

EXAMPLES

Example 1: High Throughput Drug Screen (HTS)

Culture Conditions of Bacterial Strains and Eukaryotic Cell Lines

Mycobacterial strains were routinely grown in Middlebrook 7H9 broth (supplemented with 0.2% glycerol, 10% ADC and 0.05% Tween-80) or 7H10 agar plates (supplemented with 0.5% glycerol, 10% OADC). MRC-5 human lung fibroblasts were grown in MEM-medium supplemented with 10% heat inactivated fetal bovine serum (FBS), 1% non-essential amino acids and 1 mM sodium pyruvate. RAW264.7 macrophages were grown in RPMI-medium supplemented with 10% FBS. Both cell lines were grown at 37° C. with 5% CO2.

High Throughput Drug Screen (HTS)

HTS was performed using the following procedure: compounds of the Prestwick chemical library were added into 384-well microplates (Corning) at a concentration of 100 µM in 5 µl of 5% DMSO. MRC-5 cells grown to late log phase were harvested and seeded at 4000 cells/well in a volume of 35 µl into the plates using an automated microplate dispenser (multidrop combi, Thermo Scientific). Cells were allowed to adhere for 3 hours. Mid-logarithmic phase cultures of Mtb-Erdman were washed twice with complete 7H9 medium and added to the assay plates at an MOI of 10 in 10 µl of MEM medium. Plates were sealed and incubated at 37° C./5% CO2. After 72 hours, the temperature of the plates was equilibrated to room temperature (RT) for 1 hour and 5 µl of Prestoblue cell viability reagent (Life Technologies) were added. After 1 hour at RT, fluorescence was measured in a Tecan infinite M200 plate reader (excitation 570 nm, emission 590 nm).

The host cell-based high throughput screen (HTS) was performed according to the protocol described above to select compounds that protect MRC-5 lung fibroblasts from Mtb-induced cytotoxicity. In this assay, fibroblasts were infected with high multiplicities of infection (MOI of 10) in the presence of screening compounds. After 72 hours of co-incubation, the majority of infected fibroblasts are killed by wild-type Mtb strains which can be quantified by fluorescent staining. When screening a small molecule library of US Food and Drug Administration (FDA) approved drugs (Prestwick chemical library) at a concentration of 10 µM, the gastric proton-pump inhibitor (PPI) lansoprazole (LPZ) was identified as a potent hit compound that supported fibroblast survival at rates comparable to well established anti-mycobacterial drugs such as Rifampicin and Moxifloxacine (FIG. 1). Other widely used PPIs such as omeprazole and pantoprazole were also tested. LPZ, omeprazole and pantoprazole were purchased from Sigma-Aldrich. LPZS and other LPZ analogs were purchased from Santa Cruz biotechnology, Toronto Research Chemicals Inc. and Alfa Aeser. Interestingly, these drugs were inactive in the assay at concentrations up to 50 µM (FIG. 1).

Example 2: Growth of Mtb Cells in Macrophages or Fibroblasts

Intracellular Assays and MIC Determination

Quantification of Mtb cells that infect macrophages or fibroblasts was performed using an Mtb-Erdman strain expressing GFP. For fluorescent microscopy, RAW264.7 macrophages were seeded on round 9 mm cover slips in 24 well plates ($10^5$ cells/well). For the quantification of intracellular Mtb, macrophages were infected at an MOI of 2 for 12 hours. Cells were washed several times to remove unphagocytosed bacteria and fresh medium containing compounds or DMSO was added. After incubation for four days, the cells were washed and fixed with 4% paraformaldehyde/PBS and stained with Dapi-Fluoromount-G (SouthernBiotech). Images were acquired on a Zeiss LSM 700 using ZEN imaging software and Fiji processing software. REMA assays were performed in 7H9 broth using a starting OD of 0.0001, a 7-day incubation period and a final volume of 10% resazurin (0.025% w/v).

Figure 2A:
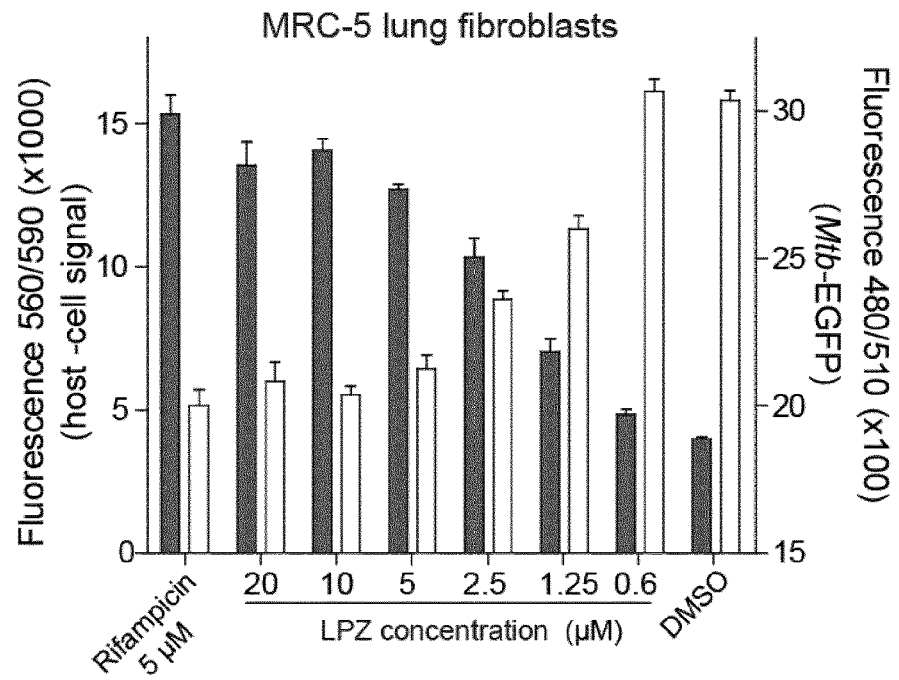
FIG. 2. A) Dose-response of LPZ in the fibroblast survival assay using mycobacteria expressing GFP. Gray bars display host-cell survival, white bars quantify intracellular Mtb-GFP. B) Dose-response of LPZ in Mtb infected RAW264.7 macrophages. Gray bars display host-cell survival, white bars quantify intracellular Mtb-GFP. C) Dose-response curve of LPZ against Mtb H37Rv in 7H9 broth.
Figure 2B:
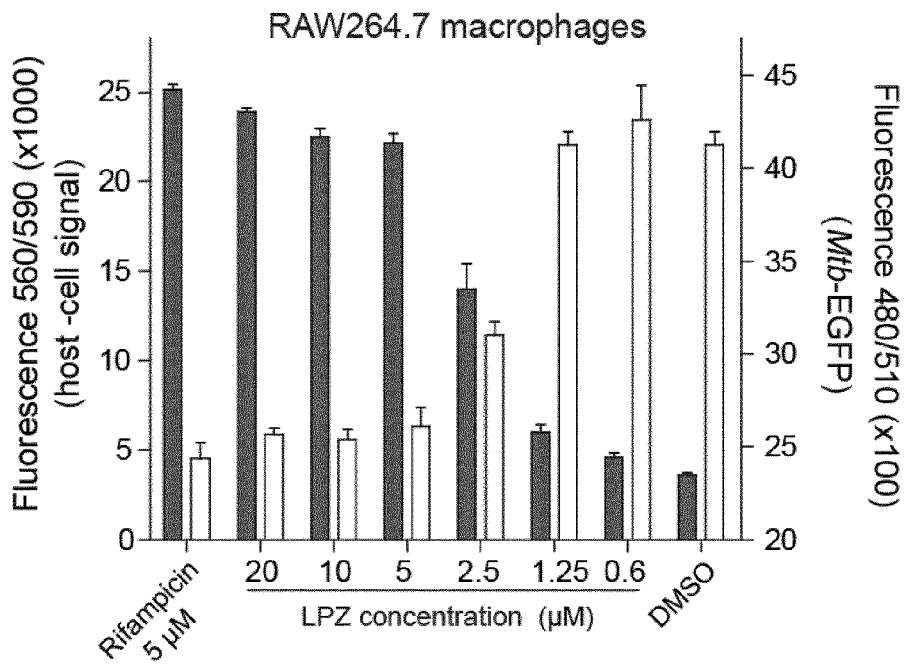
Figure 2C:
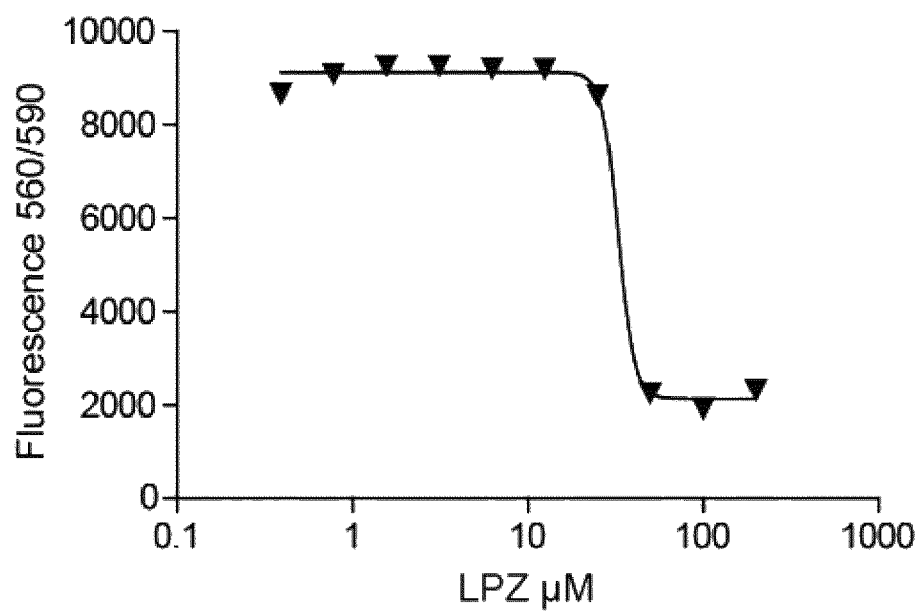

The growth of intracellular Mtb cells expressing GFP was tested at different drug concentrations. LPZ reduced the Mtb-GFP signal in a dose dependent manner with an IC50 of 1.47 µM and this correlates with the protection of MRC-5 cells (FIG. 2A). Infection experiments were also performed using RAW264.7 macrophages in which growth of intracellular bacteria was inhibited with an IC50 of 2.2 µM (FIG. 2B). In contrast to these results, the antimycobacterial activity of LPZ in common mycobacterial growth medium (7H9 supplemented with ADC) was approximately 16 times higher compared to the intracellular activity (IC50 of 32.8 µM) (FIG. 2C).

Example 3: LPZ is Converted to Lansoprazole Sulfide (LPZS) in Intracellular Environment In Vitro Pharmacokinetics and Electrospray-Ionisation Mass Spectrometry For intracellular drug quantification, 20000 MRC-5 cells were seeded in 96 well plates and exposed to 2 µM of LPZ. At given time-points, cells were extensively washed with PBS and lysed with 0.1% Triton X-100 in PBS and acetonitrile (1:1 ratio). After spinning at 15,000 g at 4° C., samples were shock frozen in liquid nitrogen and stored at −80° C. for MS.

Quantification in 7H9 broth was performed with 500 nM of LPZ, acetonitrile was added in a 1:1 ratio at given time-points followed by spinning and shock freezing. The UPLC separation was done on an Agilent 1290 Infinity LC system including the 1290 Infinity LC system Binary Pump with integrated degasser, the High Performance Autosampler and a thermostatted column compartment. The samples (2 µL) were injected into a Zorbax Extend-C18 (2.1×50 mm, 1.8 µm) analytical column operated at 40° C., using H2O—HCOOH 0.1% and CH3CN—HCOOH 0.1% as mobile phases A and B (2 to 100% B in 5 min) at a flow rate of 0.4 mL/min. The UPLC system was interfaced with a 6530 Accurate-Mass Q-TOF LC/MS system (Agilent Technologies). Electrospray-ionisation MS data were acquired in the positive ionization mode, in the mass range m/z 100-1000 (2 spectra/s). Experimental parameters were set as follows: Fragmentor: 190V, Vcap: 3500 V, gas temperature: 300° C., sheath gas temperature: 350° C. External calibration was carried out with a solution of ESI_L (Agilent). Data were processed using MassHunter.

The intracellular LPZ and possible metabolites were quantified at different time-points over a period of 48 hours using LC/MS. A rapid intracellular decay of LPZ and its conversion to a molecule of lower mass of 354 g/mol was observed (FIG. 3A/B). Interestingly, this conversion happened almost in a 1:1 ratio (FIG. 3A). When running standards of LPZ analogs in parallel experiments it was possible to identify this compound as lansoprazole sulfide (LPZS), which is both, a highly stable LPZ metabolite with no activity towards the human proton pump and a precursor of the LPZ production process.

In mycobacterial growth medium, the results were markedly different. A rapid decay of LPZ was also observed confirming the instability of this drug. However, though LPZS was detectable in increasing amounts over time, it was not the major product of LPZ decay (FIG. 3C). Assuming that LPZS is the active antimycobacterial metabolite of LPZ, this differential pattern of LPZ decay can explain the better activity of the compound during intracellular infection.

Figure 3D:
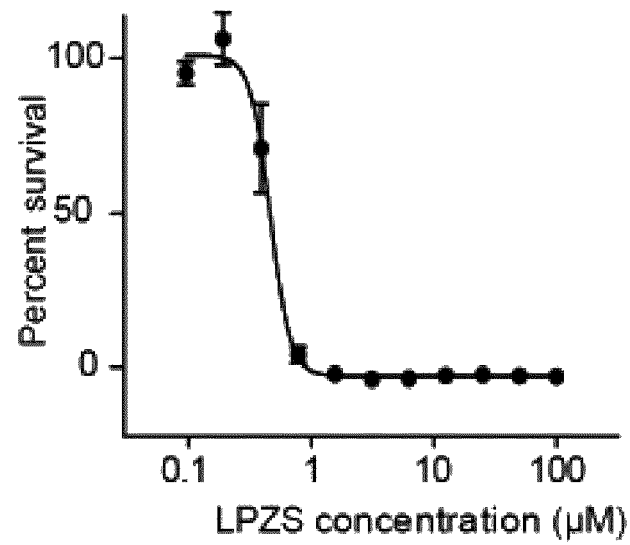
Figure 3E:
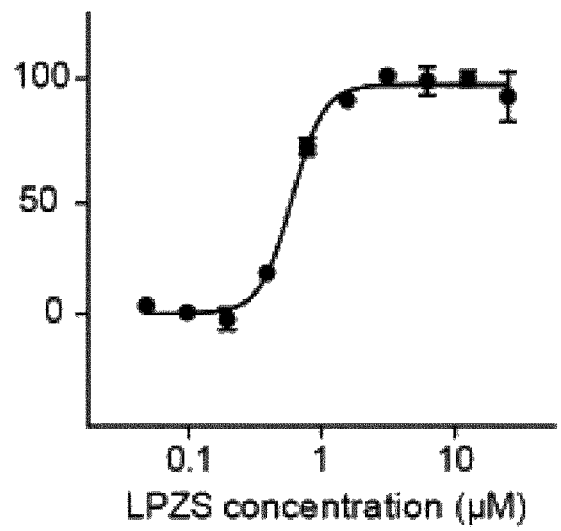

LPZS was tested for growth inhibition in broth and intracellular assays. In these experiments, the discrepancy between ex vivo and in vitro activity was not observed (FIG. 3D/E). Strikingly, LPZS had strongly improved activity over LPZ in broth at IC50 of 0.46 µM (FIG. 3D) and showed similar intracellular activity at IC50 of 0.59 µM (FIG. 3E). Thus, LPZ is a prodrug that is converted intracellularly to the antimycobacterial drug LPZS which is a potent inhibitor of mycobacterial growth.

Example 4: Activity of Benzimidazole Sulfide Derivative of General Formula (I)

Different benzimidazole sulfide derivatives of general formula (I) were tested in the intracellular assay and in the assay of Mtb growth in broth. The IC50 was determined in both assays.

TABLE 1

| Structure | IC50 intracellular | IC50 against Mtb in broth |
|---|---|---|
| 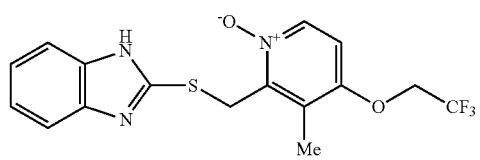<br>Lansoprazole-sulfide | 590 nM | 460 nM |
| Lansoprazole sulfide N-Oxide | inactive | 25 µM |

TABLE 1-continued
| Structure | IC50 intracellular | IC50 against Mtb in broth |
|---|---|---|
| | 3 µM | 5 µM |
| 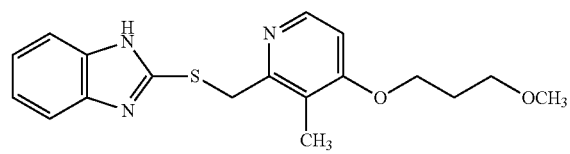  Rabeprazole sulfide | | |
| | 6 µM | 6-12 µM |
| 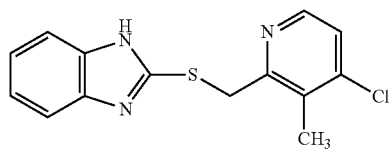  4-Desmethoxypropoxyl-4-chloro Rabeprazole Sulfide | | |
| 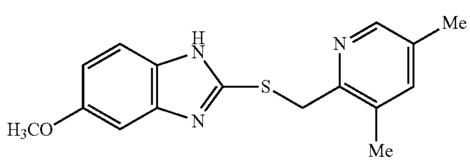 | inactive | inactive |
| 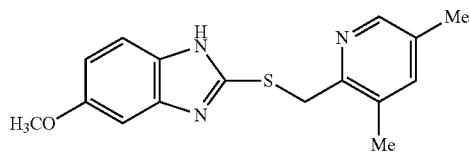  Omeprazole sulfide | | |
| 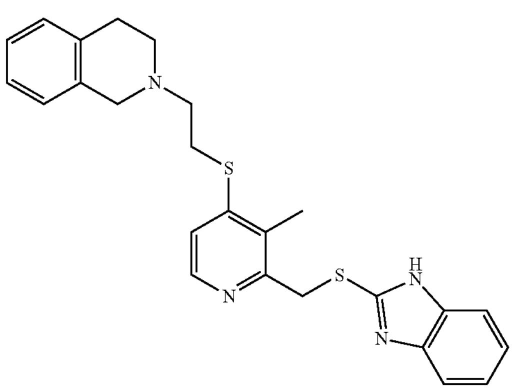 | n.d. | 2.7 µM |
| 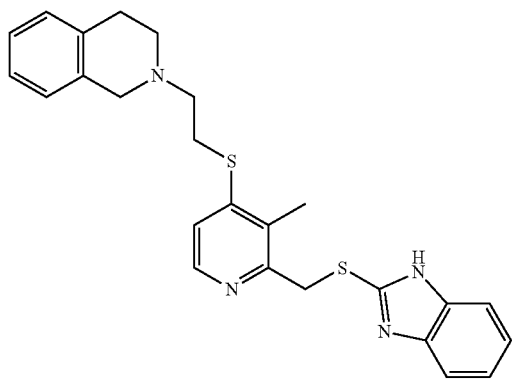  BG-28  $C_{25}H_{26}N_4S_2$  446.63 | | |

TABLE 1-continued

| Structure | IC50 intracellular | IC50 against Mtb in broth |
|---|---|---|
| 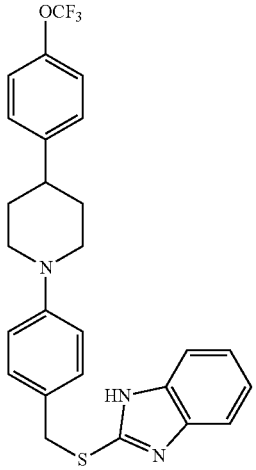<br>BG-21<br>C$_{26}$H$_{24}$F$_3$N$_3$OS<br>483.55<br>2.6 mg | n.d. | Approx. 48 µM | n.d.: not determined

Example 5: Activity of Compounds of Formula II and Further Lansoprazole Analogs

Metabolites of LPZ for activity against Mtb were tested in the intracellular assay and in the assay of Mtb growth in broth. Compounds of formula II such as Lansoprazole, its enantiomers R-lansoprazole, S-lansoprazole and the salt Rabeprazole sodium inhibit Mtb and have an IC50 below 40 µM.

In contrast, other compounds that are not compound of formula II, such as the salt of 5-hydroxy Lansoprazole potassium as well as Omeprazole and Pantoprazole were inactive in both ex vivo and in vitro assays. These compounds have substitutions on the benzimidazole ring.

TABLE 2

| Structure | IC50 intracellular | IC50 against Mtb in broth |
|---|---|---|
| 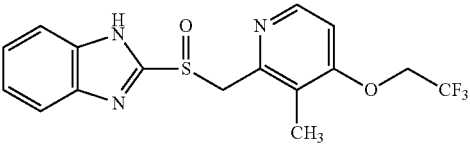<br>Lansoprazole | 1.47 µM | 32.8 µM |
| 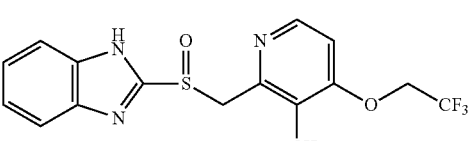<br>R-lansoprazole | 1.47 µM | 32.8 µM |
| 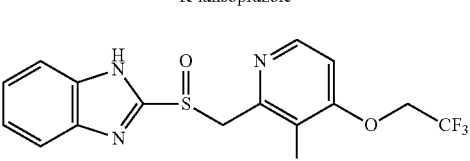<br>S-lansoprazole | 1.47 uM | 32.8 µM |

TABLE 2-continued

| Structure | IC50 intracellular | IC50 against Mtb in broth |
|---|---|---|
| 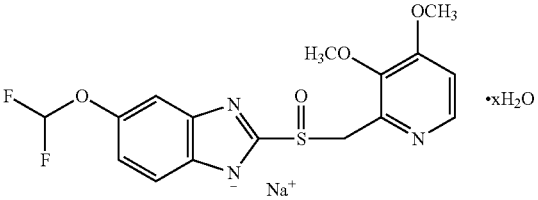<br>Pantoprazole sodium salt | Inactive | Inactive |
| 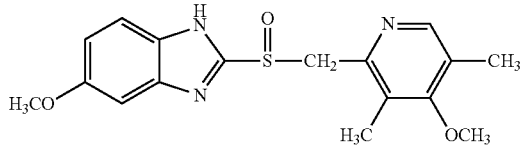<br>Omeprazole | Inactive | Inactive |
| 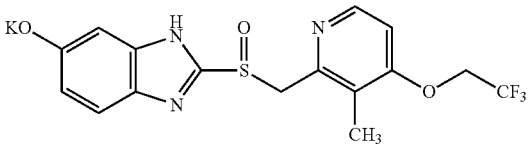<br>5-Hydroxy Lansoprazole potassium salt | Inactive | Inactive |
| 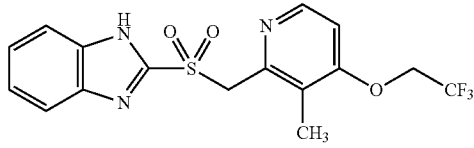<br>Lansoprazole sulfone | Inactive | Inactive |
| 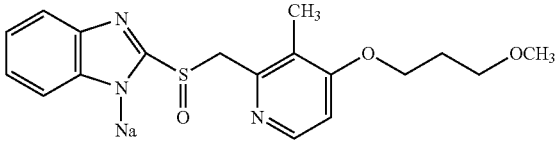<br>Rabeprazole sodium | 6 µM | 25 µM |

Example 6: Activity of LPZS Against a Selection of Mycobacterial and Non-Mycobacterial Strains Culture Conditions and REMA Assay of Non-Mtb Strains Mycobacterium strains were grown in 7H9 broth (Difco) supplemented with Middlebrook albumin-dextrose-catalase (ADC) enrichment, 0.2% glycerol, 0.05% Tween 80. *Bacillus subtilis, Candida albicans, Corynebacterium glutamicum* ATCC13032, *Escherichia coli* K12, *Micrococcus luteus, Pseudomonas putida, Salmonella typhimurium* and *Staphylococcus aureus* were grown in Luria broth base (Sigma). *Corynebacterium diphtheriae, Enterococcus faecalis, Listeria monocytogenes* and *Pseudomonas aeruginosa* were grown in brain heart infusion broth (Difco). Two-fold serial dilutions of each test compound were prepared in 96-well plates containing bacteria in a total volume of 100 µl and then incubated at 37° C. or 30° C. (depend on the strain) before addition of 10 µl of 0.025% resazurin. After incubation, fluorescence of the resazurin metabolite resorufin was determined (excitation at 560 nm and emission at 590 nm, Gain 80) by using a TECAN Infinite M200 microplate reader.

TABLE 3

| Bacteria | MIC (µM) |
|---|---|
| *Mycobacterium tuberculosis* H37Rv | 1.13 |
| *Mycobacterium tuberculosis* Erdman | 1.21 |
| *Mycobacterium tuberculosis* HN878 (Beijing strain) | 1.74 |
| *Mycobacterium abcessus* 2005-0524 | >100 |
| *Mycobacterium avium* | >100 |
| *Mycobacterium bolletii* 1999-0888 | >100 |
| *Mycobacterium marinum* M | 100 |
| *Mycobacterium massiliense* 2005-0484 | >100 |
| *Mycobacterium smegmatis* mc2155 | >100 |
| *Mycobacterium vaccae* ATCC 15483 | >100 |
| *Pseudomonas aeruginosa* | >100 |
| *Pseudomonas putida* | >100 |

TABLE 3-continued

| Bacteria | MIC (µM) |
|---|---|
| Salmonella typhimurium | >100 |
| Staphylococcus aureus | >100 |
| Bacillus subtilis | >100 |
| Candida albicans | >100 |
| Corynebacterium diphtheriae | >100 |
| Corynebacterium glutamicum | >100 |
| Enterococcus faecalis | >100 |
| Escherichia coli | >100 |
| Listeria monocytogenes | >100 |
| Micrococcus Luteus | >100 |

Interestingly, LPZS has a highly Mtb-selective activity profile with good activity against Mtb strains such as *Mycobacterium tuberculosis* H37Rv, *Mycobacterium tuberculosis* Erdman and *Mycobacterium tuberculosis* HN878 (Beijing strain) at a MIC less than 2 µM (Table 3). In contrast, the MIC was over 100 µM for other non-Mtb strains such as for *Mycobacterium abcessus* 2005-0524 or *Escherichia coli*.

Example 7: Activity of LPZS Against Drug Resistant Clinical Isolates

TABLE 4

| Clinical isolate ID | Resistance | MIC (µM) |
|---|---|---|
| M. tuberculosis 59744 | INH, RIF | 0.78 |
| M. tuberculosis MB3649 | INH | 1.37 |
| M. tuberculosis MI1020 | INH, Streptomycin | 0.94 |
| M. tuberculosis 43061 | INH | 0.49 |
| M. tuberculosis 45776 | INH | 0.52 |
| M. tuberculosis 49975 | INH | 1.06 |

Interestingly, LPZS has a highly Mtb-selective activity profile with good activity against drug resistant isolates at a MIC less than 2 µM (Table 4).

Example 8: Mice Acute Infection Model of Tuberculosis

For in vivo efficacy studies mice, BALB/c mice (18-20 g; 4 mice per group) were aerosol infected with Mtb-H37Rv and treated the following day with LPZS 300 mg/kg twice a day for 9 days. The day after final treatment, mice were sacrificed and serial dilutions of lung homogenates were plated on 7H10 agar containing 10 µg/ml cycloheximide and 25 µg/ml ampicillin.

Figure 4:
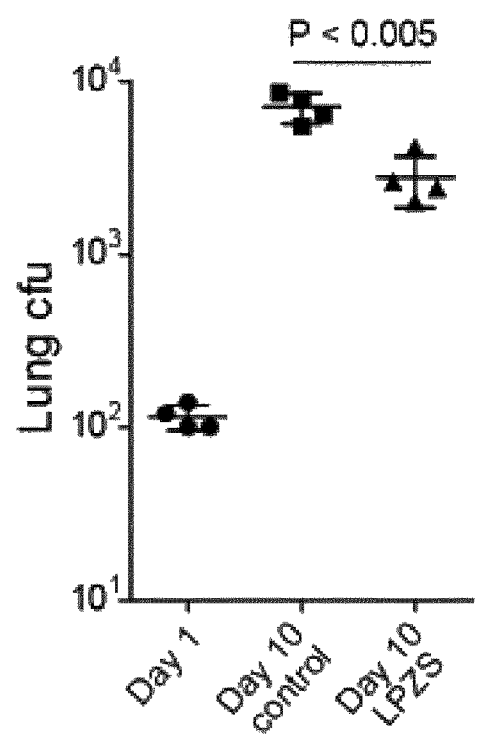
FIG. 4. Efficacy of LPZS in the mouse model of acute tuberculosis. Bacterial burden (cfu) was determined in the lungs of mice treated with the vehicle control D-α-Tocopherol polyethylene glycol 1000 succinate (TPGS) or LPZS at 300 mg/kg twice a day (mean±SD).

In the Mice acute infection model of tuberculosis, the compound LPZS significantly reduced the bacterial burden of Mtb-infected mice (FIG. 4).

Cytotoxicity of LPZS on THP1 macrophages, human liver hepatoma cells (HuH7-D12), human lung epithelial carcinoma cells (A549) and human embryonic liver cells (HepG2) (Table 5).

TABLE 5

| | THP-1 | | HuH7-D12 | | A549 | | HepG2 | |
|---|---|---|---|---|---|---|---|---|
| | TD99 | TD50 | TD99 | TD99 | TD50 | TD50 | TD99 | TD50 |
| LPZS (µM) | >100 | 75 | >100 | >100 | >100 | 37.5 | 100 | 25 |

There were no signs of toxicity in mice treated with LPZS doses as high as 300 mg/kg twice a day owing to the favourable cytotoxicity profile of LPZS (Table 5).

Example 9: Pharmacokinetics of LPZS

For pharmacokinetic studies BALB/c mice (18-20 g) were given 100 mg/kg or 300 mg/kg LPZS in 20% TPGS (D-α tocopheryl polyethylene glycol 1000 succinate). At given time-points, blood from 3 mice was taken and, after spinning, serum was treated with acetonitrile (1:4 ratio). After a second spin, supernatants were frozen for LC/MS experiments.

BALB/c mice were given 100 mg/kg or 300 mg/kg of LPZS by oral gavage and serum levels were determined after 0.5, 1, 2, 4, 8 and 24 hours (FIG. 5).

TABLE 6

| time | LPZS 300 mg/kg | | | LPZS 100 mg/kg | | |
|---|---|---|---|---|---|---|
| (hours) | mouse 1 | mouse 2 | mouse 3 | mouse 4 | mouse 5 | mouse 6 |
| 0 | 0 | 0 | 0 | 0 | 0 | 0 |
| 0.5 | 6756 | 6416 | 8354 | 2346 | 2228 | 2907 |
| 1 | 1393 | 1278 | 2283 | 484.4378 | 444.8249 | 793.9235 |
| 2 | 1321 | 996 | 743 | 459.0981 | 346.6247 | 258.3977 |
| 4 | 2816.922 | 2638.972 | 2507.601 | 905.1904 | 1134.282 | 722.1395 |
| 8 | 1622.691 | 2043.333 | 2202.665 | 415.8849 | 424.4725 | 170.2264 |
| 24 | 6.738747 | 6.998759 | 6.704449 | 7.458679 | 6.940942 | 9.317959 |

The concentration in blood of the benzimidazole sulfide derivative of formula I, lansoprazole sulfate LPZS, is 100% of Cmax at 0.5 h after administration. Thus, the pharmacokinetic profile of the benzimidazole sulfide derivatives of general formula (I) such as LPZS is favorable for a fast onset of action of these compounds.

Example 10: A Single-Nucleotide Polymorphism (SNP) in the Cytochrome bc1 Complex of Mtb Confers LPZS Resistance Isolation and Characterization of LPZS-Resistant Mtb Clones LPZS-H37Rv mutants were isolated by plating $10^9$ CFU on 7H10 agar containing 20 µM of LPZS. Whole genome sequencing of three LPZS resistant clones was performed using Illumina technology (DNA extraction methods are described in the supplemental information). Genomic DNA fragment sequencing libraries were prepared using the NEBnext Ultra DNA kit (New England Biolabs) according to the protocol supplied using 1 μg of genomic DNA. The resulting genomic DNA fragment library was loaded on Illumina MiSeq Reagent Kit V3 cartridges and sequenced.

All Illumina reads were right-trimmed to a length of 150 nucleotides to remove low quality areas. Each sample was downsampled to 1.5 M read pairs to even the genome coverages between samples. Analysis was done with MIRA (version 4.0rc4) using the Mtb H37Rv genome (NC_000962.3) as reference. The resulting SNP table was parsed in Excel for the identification of informative SNPs.

Protein Structure Prediction

QcrB (Rv2196) from *M. tuberculosis* was modeled using the software iTasser (http://zhanglab.ccmb.med.umich.edu/I-TASSER/) and the cytochrome bcl structure from the photosynthetic bacterium *Rhodobacter sphaeroides* as template (PDB code 1QJY).

Figure 6A:
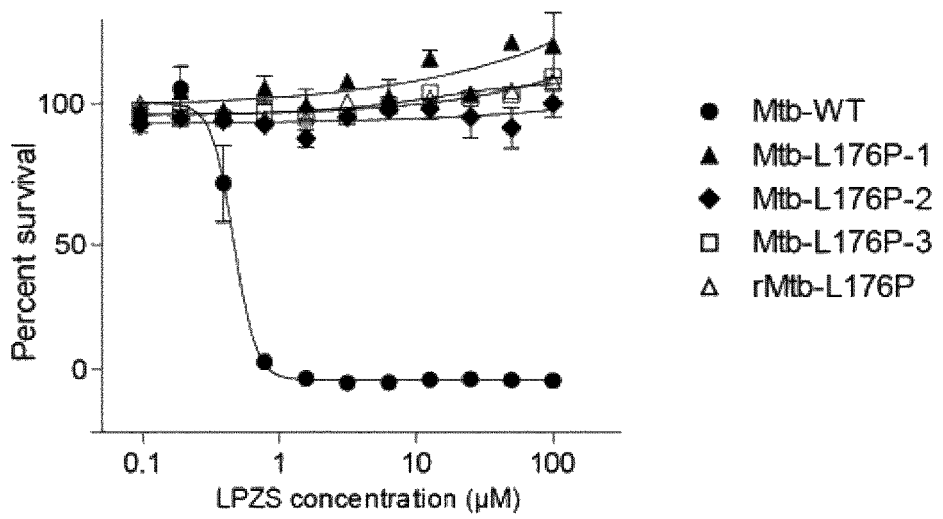
FIG. 6. LPZS targets the b subunit of the cytochrome bc1 complex. A) Dose-response of LPZS against wild-type Mtb, spontaneous-resistant mutants 1 to 3 and the genetically engineered recombinant L176P strain (rMtb-L176P). B) Dose-response curve of Q203 against wild-type Mtb, the L176P mutant and the T313A mutant which confers high level resistance to Q203. C) Dose-response curve showing that the T313A mutation does not confer high level resistance to LPZS.
Figure 6B:
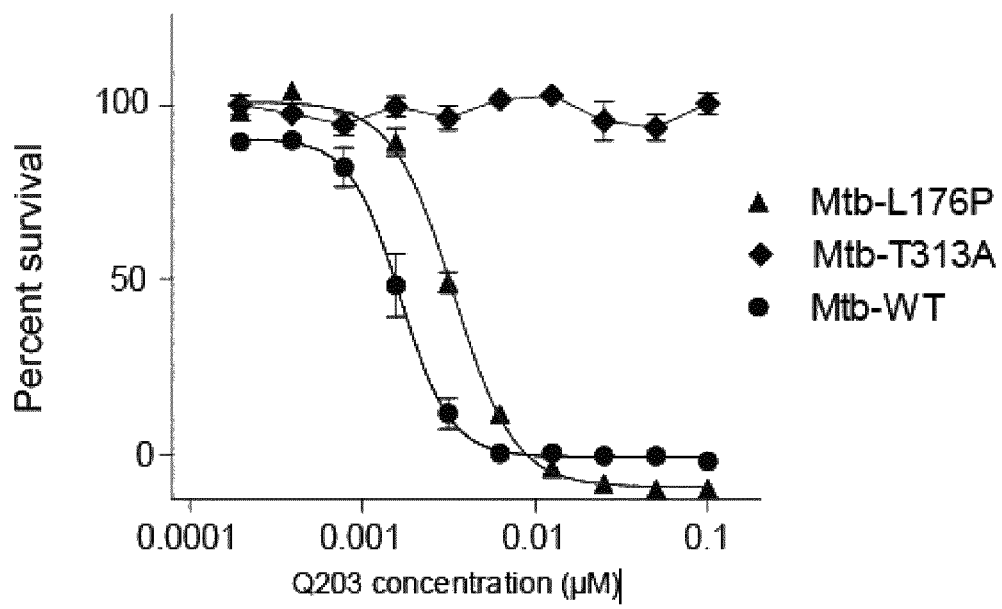
Figure 6C:
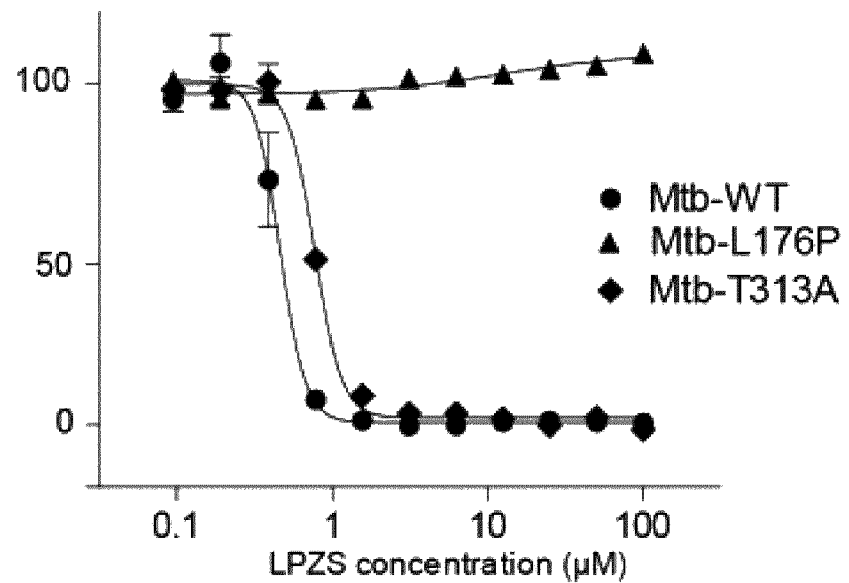

On 7H10-OADC agar plates containing 20 μM of compound, three drug resistant mutants were identified which displayed stable phenotypic resistance against LPZS (FIG. 6A). By whole genome sequencing, the same SNP in the b-subunit of the cytochrome bcl complex (qcrB, Rv2196) was identified for all three mutants leading to the amino acid change leucine-176 to proline. To confirm this mutation as the main cause for drug resistance against LPZS, the SNP was re-introduced into the genome of wild-type Mtb using homologous recombination which led to a similar shift in activity (FIG. 6A, rMtb-L176P strain). The cytochrome bcl complex (complex III) is an essential part of the mycobacterial respiratory chain. It is also the target of recently identified imidazopyridine amide compounds such as Q203 which display potent in vitro and in vivo activity against Mtb. To localize both, the L176P mutation and the T313A mutation that leads to Q203 resistance (FIG. 6B), a model of the mycobacterial QcrB protein was made on the previously published structures of *Rhodobacter sphaeroides*. Both mutations localized to the ubiquinol oxidation (Qp) site close to the Qp-inhibitor stigmatellin which was co-crystalized with the *R. sphaeroides* protein indicating that both compounds target the same QcrB active site. Remarkably, the dose-response curve shows that the T313A mutation does not confer high level resistance to LPZS. LPZS is active against the mutant Mtb-T313A that is resistant to Q203 (FIG. 6C).

The invention claimed is:

1. A method of treating tuberculosis in a subject comprising administering to a subject in need thereof a therapeutically effective amount of a benzimidazole sulfide derivative of general formula (I):

(I)

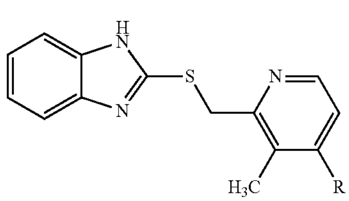

wherein R is selected from the group consisting of hydrogen, $C_1$-$C_6$-alkyl, $C_1$-$C_6$-heteroalkyl, $C_1$-$C_6$-haloalkyl, aryl, $C_1$-$C_6$-alkyl aryl, heteroaryl, $C_1$-$C_6$-alkyl heteroaryl, $C_2$-$C_6$-alkenyl, $C_2$-$C_6$-alkenyl aryl, $C_2$-$C_6$-alkenyl heteroaryl, $C_3$-$C_8$-cycloalkyl, $C_1$-$C_6$-alkyl cycloalkyl, heterocycloalkyl, $C_1$-$C_6$-alkyl heterocycloalkyl, carboxy, $C_1$-$C_6$-alkyl carboxy, acyl, $C_1$-$C_6$-alkyl acyl, acyloxy, $C_1$-$C_6$-alkyl acyloxy, alkoxy, $C_1$-$C_6$-alkoxy, $C_1$-$C_6$-heteroalkoxy, $C_1$-$C_6$-haloalkoxy, $C_1$-$C_6$-alkoxycarbonyl, halogen, sulfanyl, and $C_1$-$C_6$-alkylsulfanyl, a pharmaceutically acceptable salt thereof, and/or a mixture thereof.

2. The method according to claim 1, wherein R is selected from the group consisting of $C_1$-$C_6$-alkyl, $C_1$-$C_6$-heteroalkyl, $C_1$-$C_6$-haloalkyl, $C_1$-$C_6$-alkoxy, $C_1$-$C_6$-heteroalkoxy, $C_1$-$C_6$-haloalkoxy, and halogen.

3. The method according to claim 1, wherein the tuberculosis is caused by a bacterial strain selected from the group consisting of a mycobacterial, strain and a multi-drug resistant strain of *mycobacterium*.

4. The method according to claim 3, wherein the mycobacterial train is selected from the group consisting of *M. Tuberculosis* H37Rv, *M. Tuberculosis* Erdman, and *M. Tuberculosis* HN878.

5. The method according to claim 3, wherein the multi-drug resistant strain of *mycobacterium* is selected from the group consisting of *M. Tuberculosis* 59744*, M. Tuberculosis MB*3649*, M. Tuberculosis* MI1020*, M. Tuberculosis* 43061*, M. Tuberculosis* 45776, and *M. Tuberculosis* 49975.

6. The method according to claim 1, wherein said benzimidazole sulfide derivative is selected from the group consisting of:

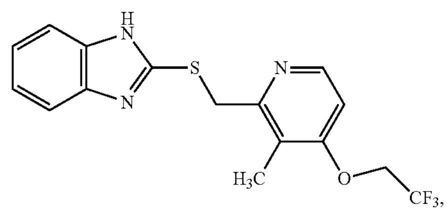

,

, and

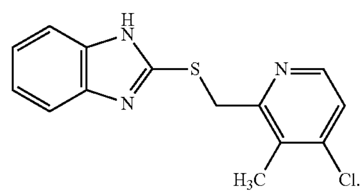

.

7. The method according to claim 1, wherein said benzimidazole sulfide derivative has an IC50 less than about 20 μM.

8. The method according to claim 1, wherein the concentration in blood of said benzimidazole sulfide derivative is at least 50% of Cmax at 0.5 hours after administration.

9. The method of claim 1, wherein said benzimidazole sulfide derivative is administered to said subject in the form of a pharmaceutical composition comprising the benzimidazole sulfide derivative and a pharmaceutically acceptable carrier, diluent or excipient.

10. The method according to claim 9, wherein the pharmaceutical composition further comprises one or more additional agents effective against tuberculosis infection.

11. The method according to claim 10, wherein the one or more additional agents effective against tuberculosis infection is selected from the group consisting of rifampin, moxifloxacin, isoniazid, rifapentine, rifabutin, pyrazinamide, ethambutol, streptomycin, kanamycin, amikacin, gatifloxacin, levofloxacin, ofloxacin, ciprofloxacin, capreomycin, ethionamide, cycloserine, para-aminosalicylic acid, thiacetazone, clarithromycin, amoxicillin-clavulanic acid, imipenem, meropenem, viomycin, terizidone, TMC207, PA-824, OPC-7683, LL-3858, and SQ-109.

* * * * *